(12) United States Patent
Bernick et al.

(10) Patent No.: US 8,577,716 B2
(45) Date of Patent: Nov. 5, 2013

(54) SYSTEM AND METHOD OF ONGOING EVALUATION REPORTING AND ANALYSIS

(75) Inventors: Brian Bernick, Boca Raton, FL (US); Robert Finizio, Boca Raton, FL (US); John Milligan, Middleburg, VA (US)

(73) Assignee: TherapeuticsMD, Inc., Boca Raton, FL (US)

( * ) Notice: Subject to any disclaimer, the term of this patent is extended or adjusted under 35 U.S.C. 154(b) by 665 days.

(21) Appl. No.: 12/561,515

(22) Filed: Sep. 17, 2009

(65) Prior Publication Data

US 2011/0066473 A1    Mar. 17, 2011

(51) Int. Cl.
*G06Q 10/00* (2012.01)

(52) U.S. Cl.
USPC ............. 705/7.32; 705/2; 705/3; 705/7.29; 705/7.33

(58) Field of Classification Search
USPC ..................... 705/7.11–7.42, 2, 3
See application file for complete search history.

(56) References Cited

U.S. PATENT DOCUMENTS

| | | | | |
|---|---|---|---|---|
| 7,925,519 | B2 * | 4/2011 | Greene | 705/2 |
| 7,945,459 | B2 * | 5/2011 | Grace et al. | 705/2 |
| 2001/0032125 | A1 * | 10/2001 | Bhan et al. | 705/14 |
| 2004/0243437 | A1 * | 12/2004 | Grace et al. | 705/2 |
| 2005/0228692 | A1 * | 10/2005 | Hodgdon | 705/2 |
| 2005/0228718 | A1 * | 10/2005 | Austin | 705/14 |
| 2009/0164341 | A1 * | 6/2009 | Sunvold et al. | 705/27 |

* cited by examiner

Primary Examiner — David Rines
(74) Attorney, Agent, or Firm — Snell & Wilmer L.L.P.

(57) ABSTRACT

A research and development system that gathers feedback from patients and healthcare providers with respect to the their experience with various aspects of a supplier's products in order to tabulate, consolidate, compare and analyze the data received rapidly and efficiently, and which can be used on successive iterations to determine future products and services.

20 Claims, 12 Drawing Sheets vitaMedMD Prenatal Vitamin and DHA

| | Very Important | Somewhat Important | Not Important |
|---|---|---|---|
| 1. How important are the following in recommending vitaMedMD Prenatal Vitamin and DHA : | | | |
| A. vitaMedMD Prenatal Vitamin and DHA is a complete prenatal vitamin formula with 21 vitamins and minerals including 975mcg of folic acid. <br> Patient Specific Comment [ ] | ☐ | ☐ | ☐ |
| B. vitaMedMD Prenatal Vitamin and DHA is 100% vegetarian including a vegetarian prenatal softgel. <br> Patient Specific Comment [ ] | ☐ | ☐ | ☐ |
| C. vitaMedMD Prenatal Vitamin and DHA is the only non-fish and 100% vegetarian prenatal supplement meeting the NIH recommendations of 300mg DHA supplementation in pregnancy. <br> Patient Specific Comment [ ] | ☐ | ☐ | ☐ |
| D. vitaMedMD Prenatal Vitamin and DHA has an exclusive chelated form of iron that is more easily tolerated and absorbed by pregnant women and provides the CDC recommended amount of iron supplementation in pregnancy. <br> Patient Specific Comment [ ] | ☐ | ☐ | ☐ |
| E. vitaMedMD Prenatal Vitamin and DHA contains extra vitamin B6 to reduce pregnancy-induced nausea and fatigue. <br> Patient Specific Comment [ ] | ☐ | ☐ | ☐ |
| F. vitaMedMD Prenatal Vitamin and DHA are taken in a single daily dose of tablet and softgel. <br> Patient Specific Comment [ ] | ☐ | ☐ | ☐ |
| G. vitaMedMD Prenatal Vitamin and DHA has orange coating and flavoring of both the multivitamin and DHA softgel to eliminate aftertaste common in other supplements. <br> Patient Specific Comment [ ] | ☐ | ☐ | ☐ |

2. vitaMedMD Prenatal Vitamin contains 975mcg of Folic Acid. Prescription prenatal vitamins are negligibly different and include 1,000 mcg of Folic Acid. The recommended daily value of Folic Acid for pregnant and expecting women is 800mcg.

Yes      No

A. Are you satisfied with the Folic Acid content of the vitaMedMD Prenatal Vitamin? ☐ ☐

Patient Specific Comment [ ]

B. do you support that the 975mcg of Folic Acid in the vitaMedMD Prenatal Vitamin is ☐ ☐
Clinically insignificant from the 1,000 mcg of Folic Acid in a typical prescription prenatal vitamin?

Patient Specific Comment [ ]

C. Do you believe that the 975mcg of Folic Acid in the vitaMedMD Prental Vitamin is ☐ ☐
Important for pregnant and expectant women versus the only 800mcg of Folic Acid in most other nonprescription prenatal vitamins?

Patient Specific Comment [ ]

3. Do you prefer a DHA supplement that is plant derived and not fish-oil based, reducing the risks of ocean borne contaminants including heavy metals, PCB's, dioxins and mercury?

☐ Yes      ☐ No

Patient Specific Comment [ ]

4. Was the product well tolerated by your patients?

☐ Yes      ☐ No

Patient Specific Comment [ ]

5. Please comment if you aware of any ordering or shipping issues with respect to the product?

☐ No issues

Patient Specific Comment [ ]

6. Please provide any additional comments or suggestions regarding the products or vitaMedMD services.

No suggestions

Comment [ ]

FIG. 8b

7. How often would you recommend the following future vitaMedMD products?

|  | Frequently | Sometimes | Not Very Often |
|---|---|---|---|
| A. Chewable Prenatal Vitamins | ☐ | ☐ | ☐ |
| Comment [            ] | | | |
| B. Kosher Prenatal Vitamins | ☐ | ☐ | ☐ |
| Comment [            ] | | | |
| C. Anti-nausea/Vomiting Prenatal Vitamin | ☐ | ☐ | ☐ |
| Comment [            ] | | | |
| D. 600mg Calcium + 500 IU Vitamin D3 Calcium Chew | ☐ | ☐ | ☐ |
| Comment [            ] | | | |
| E. Isoflavones/Phytoestrogen Supplements for bone preservation and treatment of vasomotor symptoms | ☐ | ☐ | ☐ |
| Comment [            ] | | | |
| F. Multivitamin/Antioxidant | ☐ | ☐ | ☐ |
| Comment [            ] | | | |
| G. Diet Suppressant/Weight Loss Supplement | ☐ | ☐ | ☐ |
| Comment [            ] | | | |

8. Please provide any suggestions as to new products or services that you would like vitaMedMD to offer.

☐ No suggestions

Comment [            ]

9. Will you recomment vitaMedMD Prenatal Vitamin and DHA to your patients?

☐ Yes     ☐ No

Patient Specific Comment [            ]

FIG. 8c

|  | Very Important | Somewhat Important | Not Important |
|---|---|---|---|

1. How important are the following in recommending vitaMedMD Chocolate Calcium Chews:

A. vitaMedMD Chocolate Calcium Chews contians 500mg of Calcium Carbonate in each small chocolate chew. ☐ ☐ ☐

Patient Specific Comment [_____]

B. vitaMedMD Chocolate Calcium Chews contains 200 IU of vitamin D3 in each small chocolate chew. ☐ ☐ ☐

Patient Specific Comment [_____]

C. The daily recommended calcium intake may be achieved by conveniently taking only two or three vitaMedMD Chocolate Calcium Chews a day. ☐ ☐ ☐

Patient Specific Comment [_____]

D. vitaMedMD Chocolate Calcium Chews are made with real cocoa for sweet milk chocolate taste without the chalky and bitter aftertaste of the other brands. ☐ ☐ ☐

Patient Specific Comment [_____]

E. Future vitaMedMD Chocolate Calcium Chews will include <u>600mg</u> of Calcium and <u>500</u> IU of Vitamin D3 in each chocolate chew. ☐ ☐ ☐

2. Was the product well tolerated by your patients?

☐ Yes    ☐ No

Please comment in the space below if your patients had any adverse events.

Patient Specific Comment [_____]

3. Please comment if you aware of any ordering or shipping issues with respect to the product?

☐ No issues

Patient Specific Comment [_____]

4. Please provide any additional comments or suggestions regarding the Products or vitaMedMD services.

☐ No suggestions

Patient Specific Comment [_____]

| 5. How often would you recommend the following future vitaMedMD products: | Frequently | Sometimes | Not Very Often |
|---|---|---|---|
| A. 600mg Calcium + 500 IU Vitamin D3 Calcium Chew | ☐ | ☐ | ☐ |
| Comment [          ] | | | |
| B. Isoflavones/Phytoestrogen Supplements for bone preservation and treatment of vasomotor symptoms | ☐ | ☐ | ☐ |
| Comment [          ] | | | |
| C. Multivitamin/Antioxidant | ☐ | ☐ | ☐ |
| Comment [          ] | | | |
| D. Diet Suppressant/Weight Loss Supplement | ☐ | ☐ | ☐ |
| Comment [          ] | | | |
| E. Chewable Prenatal Vitamin | ☐ | ☐ | ☐ |
| Comment [          ] | | | |
| F. Kosher Prenatal Vitamin | ☐ | ☐ | ☐ |
| Comment [          ] | | | |
| G. Anti-nausea/Vomiting Prenatal Vitamin | ☐ | ☐ | ☐ |
| Comment [          ] | | | |

6. Please provide any suggestions as to new products or services that you would like vitaMedMD to offer.

☐ No suggestions

Comment [          ]

7. Will you recommend vitaMedMD Chocolate Calcium Chews to your patients?

☐ Yes    ☐ No

Patient Specific Comment [          ]

FIG. 9b

SYSTEM AND METHOD OF ONGOING EVALUATION REPORTING AND ANALYSIS

BACKGROUND OF THE INVENTION

1. Field of Invention

The present invention relates to product development. It applies particularly to the analysis of feedback from customers, patients and healthcare providers to product suppliers, and will be described with particular reference thereto.

2. Background

Much of the research and development in the industry is currently done on an infrequent basis with limited customer feedback. Surveys are periodically sent out to a limited pool of customers with marginal quality feedback, relative to collection rates. This leads to lower quality products and substantial lag time in reacting to customers ever changing needs. Most companies doing traditional, episodic, and limited customer surveys take years to release new products and enhance existing products and services. This type of traditional market research and development results in: (1) limited success in discovering any gaps in the product portfolio, (2) considerable lag time in discovering product inconsistencies and quality issues, (3) prolonged development cycles, (4) poor customer satisfaction and retention, and (5) increased development cost, and therefore, increased cost to the customer.

Known solutions in the art include paper based periodic customer surveys, periodic telephone surveys, door to door/in-person surveys and periodic internet spam surveys.

The present invention produces a quicker, more accurate, statistically superior, analytically and subjective based research product development system.

The present invention is a more efficient, statistically superior, product research and development system that efficiently and continuously collects high quality analytical and subjective customer data. Moreover, the continuous monitoring aspect of the system (enabled through a computer communication system) improves productivity, while reducing cost. The present invention is superior, faster and cheaper than other research and development systems.

Additionally, this system is suitable for dietary supplements because the Food and Drug Administration does not require dietary supplements to undergo pre-market approval for safety and efficacy. Instead, the FDA relies mostly on its adverse event reporting system to identify safety problems. However, because reporting is entirely voluntary, adverse event reporting systems typically detect only a small proportion of the events that occur. One FDA-commissioned study estimated that less than 1 percent of all adverse events associated with dietary supplements are actually reported.

SUMMARY OF THE INVENTION

Throughout the description of the invention the terms "patient" and "healthcare provider," "doctor," or "physician" will be used. However, the term "patient" is defined herein to also mean other customers of supplements and healthcare services, regardless of whether a patient doctor relationship attaches. Similarly, the terms "healthcare provider," "doctor," or "physician" are defined herein to also mean other providers of healthcare services, regardless of whether a patient doctor relationship attaches.

Patients who have purchased items from a supplier whose information and email addresses are stored in the system and the above noted healthcare providers are extended email invitations to complete linked surveys.

Patients and healthcare providers report requested information via the system. Forms with questions and free text field to enter data collected are provided. Once the forms are completed, they are sent via the Internet and analyzed. This information is utilized to enhance current products/services and create new innovative products/services.

The present invention utilizes the Internet and gathers feedback from patients and healthcare providers with respect to the their experience with various aspects of a company's products and services in order to tabulate, consolidate, compare and analyze the data received which is used to determine future products and services.

The process starts with the healthcare providers receiving feedback from their patients relative to their experience with subject products. Healthcare providers are asked to gather a combination of analytical and subjective patient experience data. The healthcare providers enter this data into a form that may be accessed via the Internet. The healthcare providers also enter their own impressions and opinions relative to the subject products and services.

After the data has been fully analyzed, the information available from the system is used to determine characteristics of a future product pipeline, including enhancements to current products as well developing new product additions to the portfolio.

The reporting mechanism of the system results in measurements that help to understand the quality and capability of a product, including an index of qualities against a Six Sigma yardstick. Accordingly, this invention helps assure the development and changes to products and additional product lines based on verifiable data, rather than assumptions. As these changes come to market, the system's cycle of continuous patient and healthcare provider feedback and resultant improvement continues.

The system produces quantifiable patient and healthcare provider feedback that can be immediately implemented resulting in sustained quality improvement.

Furthermore, the present invention will accelerate the improvement in all aspects of the business process from product development to customer service by improving quality and reducing waste and defects.

The system gathers demographics from every patient and the associated healthcare provider that buys a product from the system.

The system creates survey questions for patients and healthcare providers that can be customized to a specific product or service.

The system may also identify potential survey takers by captured demographic information and extend surveys to only those whose demographics/experience would be most wanted with respect to a product or service.

The present system tabulates and analyzes the data with respect to demographics of its participants and survey responses for the company hosting and administering the system and can also be made available to any secondary client interested in aggregating specific survey response statistics through the defined pool of customers/patients and healthcare providers of the hosting company that will serve as surveyors.

The present system also provides a compensation mechanism for which an honorarium or other compensation can be provided to the surveyors to support product distribution and feedback compliance.

Accordingly, the present system will solve the lack of adverse reporting with respect to nutritional supplements. It will provide all the necessary information to evaluate an event including consumer, product, medical and manufacturer information as well as data needed to analyze any trends.

The present invention's reporting mechanism also results in specific measurements that help with understanding the qualities and capabilities of a product, and may index those qualities against a Six Sigma yardstick.

The present system is able to gather, tabulate, consolidate, compare and analyze the data received from multiple physicians.

Once the data is analyzed, the information will be used to determine the characteristics of future products created with the benefit of the information obtained by the system, including enhancements to current products and development of new product additions to a supplier's portfolio.

Accordingly, one objective of the present invention is to help assure that development and changes to current products and additional product lines are based on verifiable data, rather than assumptions. The method of continuous patient and healthcare provider feedback may result in constant product improvement.

Furthermore, the data-driven approach of the present invention allows for an accurate understanding of the customer's (patients and healthcare providers) transaction lifecycle. With this data, areas where significant value or improvement can be identified.

Another objective of the present invention is to provide accelerated product improvement in all aspects from price to product development to customer service by improving quality and reducing waste and defects.

Yet another objective of the present invention is a more efficient, statistically superior, product research and development system that efficiently and continuously collects high quality analytical and subjective customer data. Moreover, the continuous monitoring aspect of the system drastically reduces cycle time and improves productivity, while reducing cost.

Other objectives include the creation of a real time monitoring and development feedback loop between healthcare provider, patient and company erasing traditional product development gaps, elimination of current product issues and inconsistencies through constant monitoring, and elimination of lag from traditional new product to market research periods.

Other objectives include the provision of a quality feedback from critical healthcare provider constituency, continuous monitoring of customer and product success rates, provision of patient level data, consideration of analytical and subjective data to capture full customer experience, provision of the ability for a product supplier to personalize products quickly, reduction of overall cycle time for product development, provision of quick reaction time to product problems/issues, and provision of a broader customer base.

The present invention fulfills these objectives, as well as other needs and objectives, as will be apparent from the following description of the present invention. Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating preferred embodiments and are not to be construed as limiting the invention.

FIGS. 8a and 8b are a sample survey generated by the system of the invention.

FIGS. 9a and 9b are a sample survey generated by the system of the invention.

DETAILED DESCRIPTION OF THE INVENTION

Figure 1:
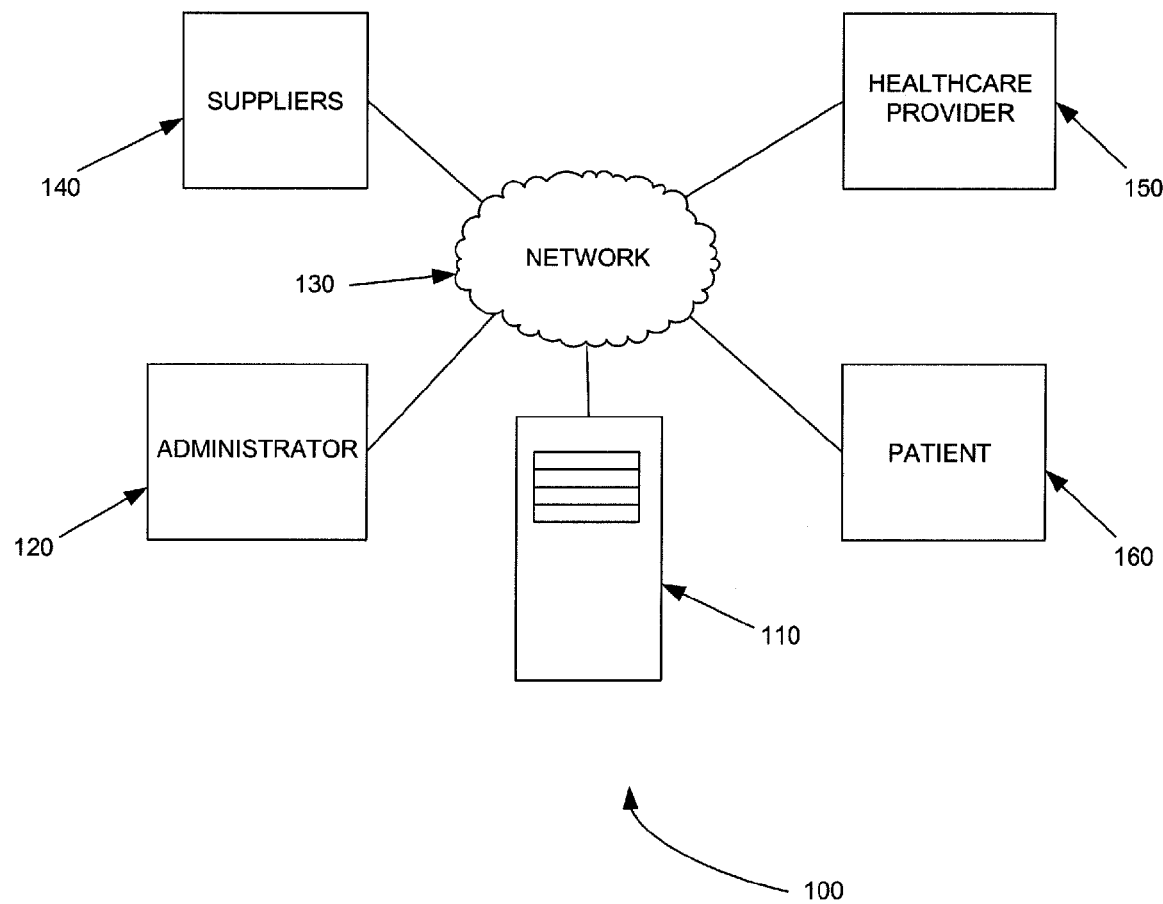
FIG. 1 is a schematic diagram of the system of the invention for the obtainment and analysis of feedback from healthcare providers and patients.

FIG. 1 schematically depicts a survey production, analysis and messaging system 100 configured for the obtainment and analysis of feedback from healthcare providers and patients. The system 100 can include a host server 110 configured for communicative coupling with an administrator 120 over a computer communications network 130 to different computing devices for different users of the system. The administrator 120 may be coupled to the host server directly or over a computer communications network 130. Similarly, the other users such as suppliers 140, healthcare providers 150 and patients 160 may be coupled to the host server 110 directly or over a computer communications network 130. The host server 110 may support the operation of the system 100; however, other means for supporting the operation of a system over a computer communications network are known in the art.

Figure 2:
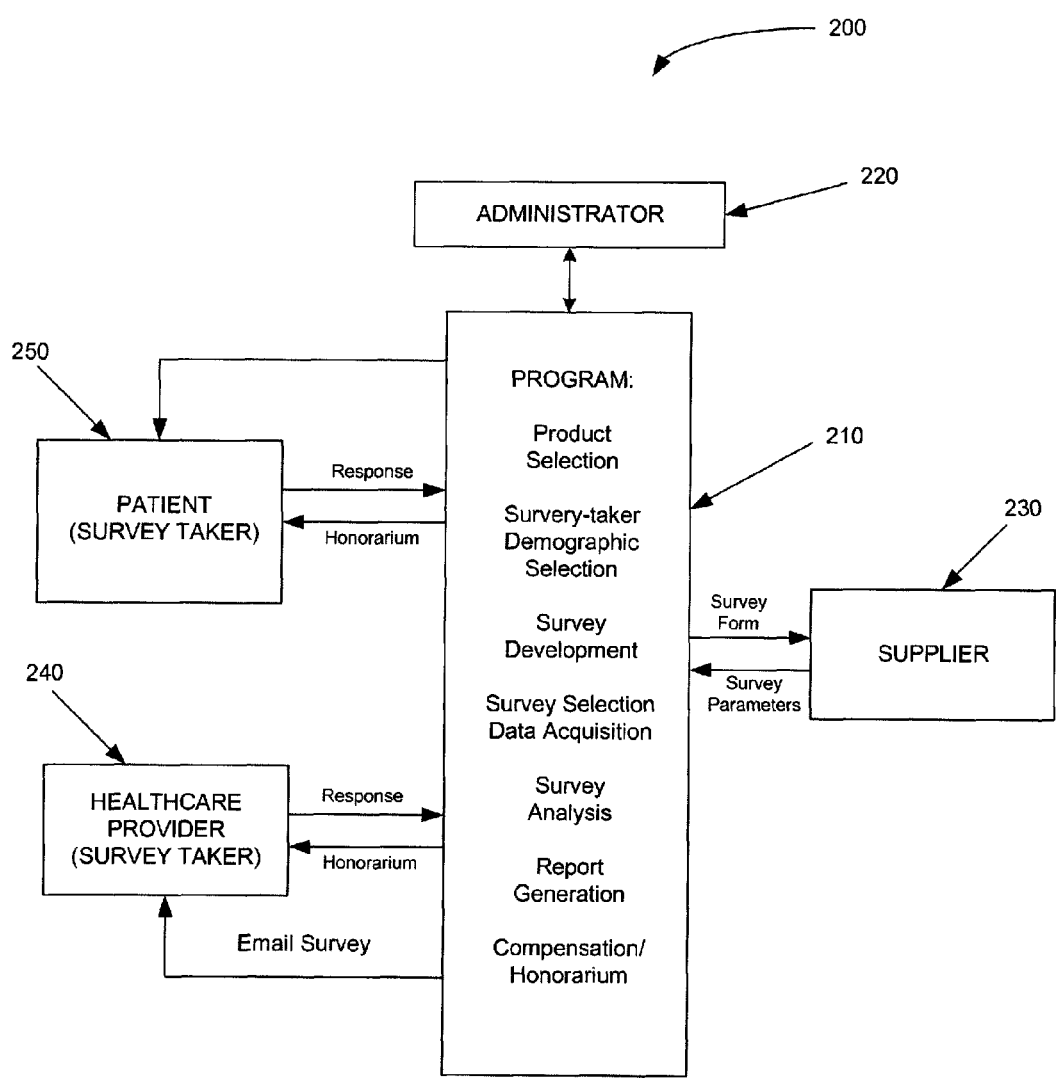
FIG. 2 is a flow chart diagram of the system of the invention for the obtainment and analysis of feedback from healthcare providers and patients.

FIG. 2 provides a general flow chart of the data flow for information in the system 200. As shown the program 210 provides interaction between the administrator 220, the supplier 230, the healthcare provider 240 and the patient 250. As shown, the program 210 includes several steps, including product selection, demographic selection, survey development, survey selection and data acquisition, survey analysis, report generation and compensation/honorarium. The supplier 230 provides survey parameters for the program 210 and the program 210 then uses that data to create a survey form for selection and editing, if needed, by the supplier 230. The survey form is then provided to the healthcare provider 240 or the patient 250, or both by means such as email or access to a web page on a computer communications network. The responses to the survey by the healthcare provider 240 or patient 250, or both, is then input into the program 210. An honorarium or other compensation may be provided to the healthcare provider 240 or patient 250, or both, for participation in one or more surveys.

In addition, the responses provide information which can lead to improvements in the product supplied to the supplier 230, and a new survey may be taken regarding the new product. Several iterations may occur, where a survey is used for one or more features of the product, resulting in a more improved product, or one or more products with more advantageous features.

Figure 3:
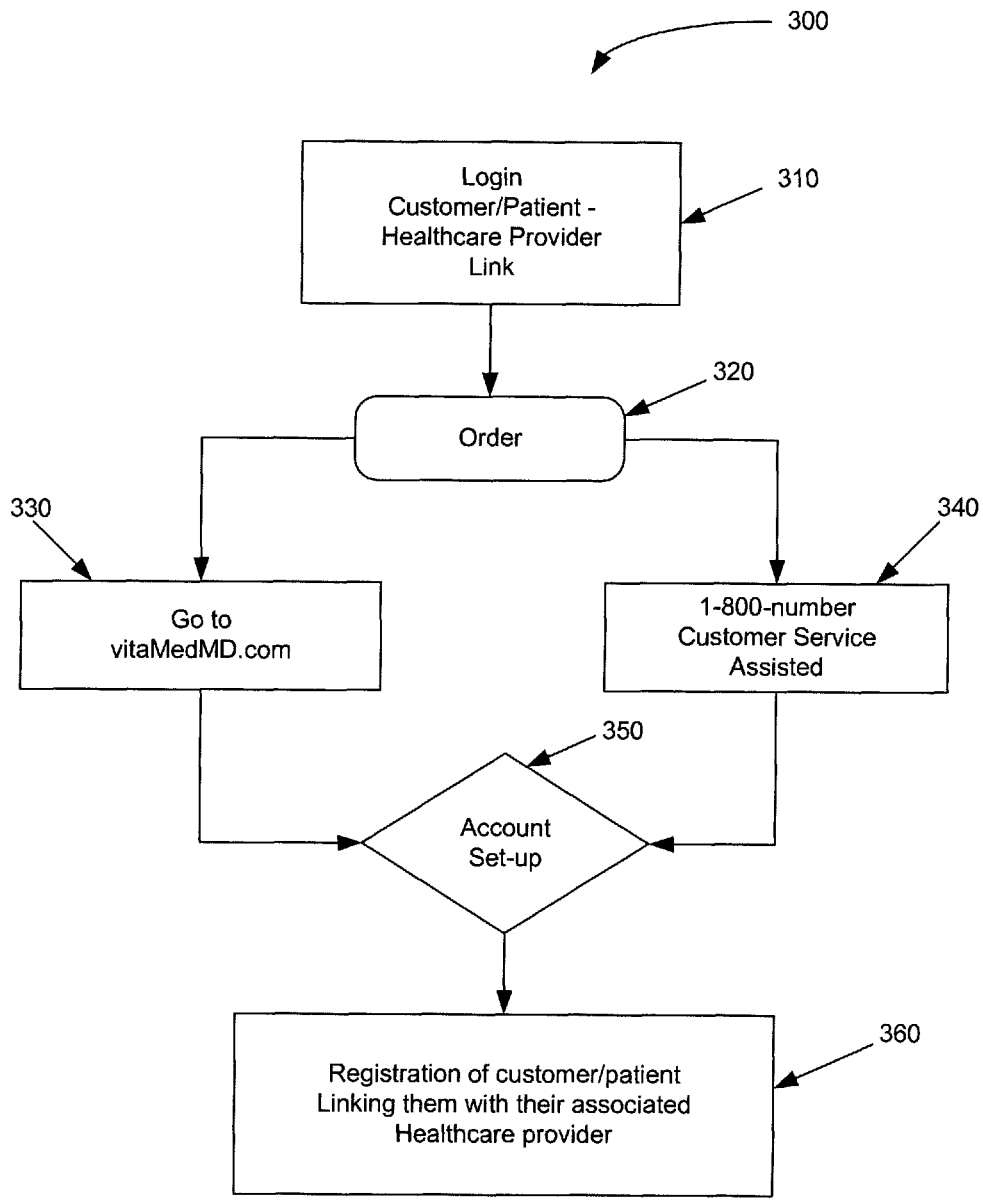
FIG. 3 is a flow chart diagram of the patient-healthcare provider link portion of the system of the invention.

FIG. 3. illustrates a login process of the system 300 for the patient in the system to connect the patient with the healthcare provider. As shown, a login screen 310 or other equivalent means for accessing the system is provided. An order 320 is made for a particular product 320 by the patient or the healthcare provider. The order 320 may be made by either visiting the administrator's or supplier's website 330 or by dialing a customer service number 340 or by equivalent means. In one embodiment, the patient is identified and correlated with the patient's healthcare provider whose identity has already been entered in the system. Once the patient has been identified as being in the care of the healthcare provider, the patient account is set up 350, and the patient is registered with the program and the patient is linked with the associated healthcare provider 360.

Figure 4:
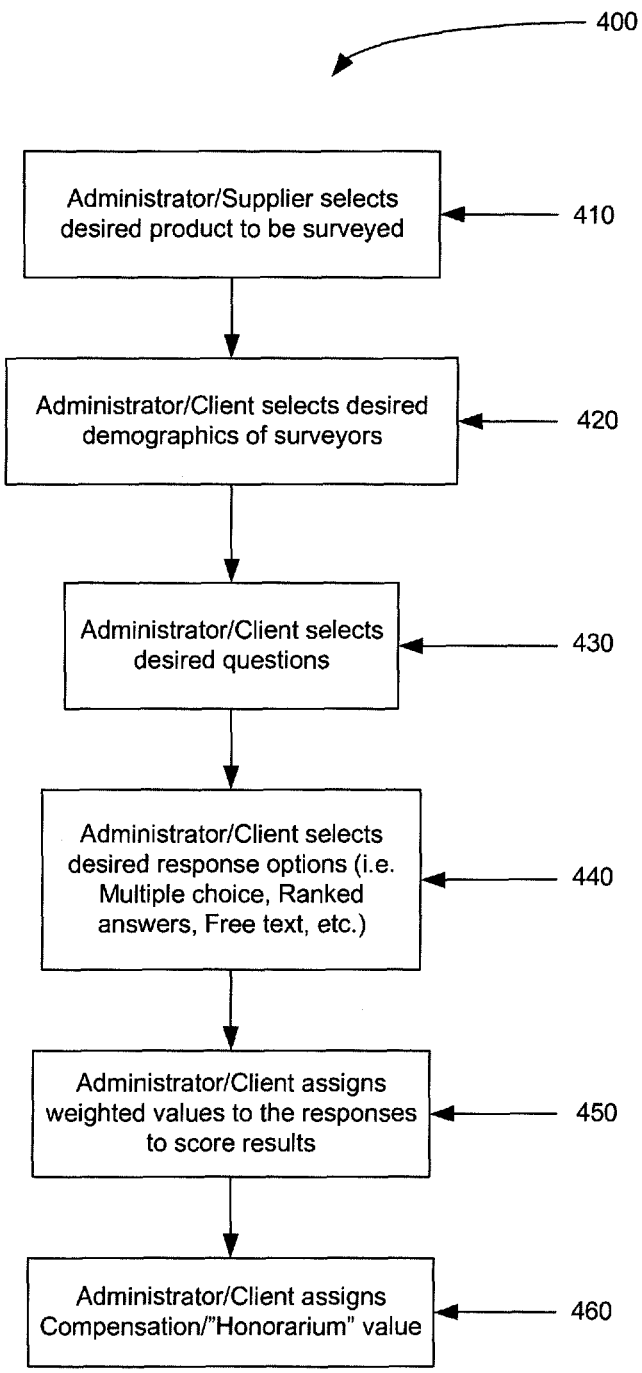
FIG. 4 is a flow chart diagram of the supplier's survey development portion of the system of the invention.

FIG. 4 illustrates the survey development portion of the system 400. In this portion, the administrator or supplier may select the product to be the subject of a survey 410. The selector then selects the desired demographics of the healthcare providers who will be responding to the surveys 420. The selector then selects desired questions 430 for the survey. The questions 430 may be included in a list, or the selector may provide original questions to be placed on the survey, or a combination may be used. If appropriate, the selector then selects the desired response options 440 for the survey taker. Such options 440 may include multiple choices, ranked answers, free text to be supplied by the survey taker, or the like. Then the selector may assign weighted values to the responses for scoring of the results 450 of the surveys. In addition, the selector may assign an honorarium or amount of compensation 460 for the healthcare provider or the patient, or both. In one embodiment, a data analysis collection and analysis program such as SharePoint may be used to prepare the survey of the system.

Figure 5:
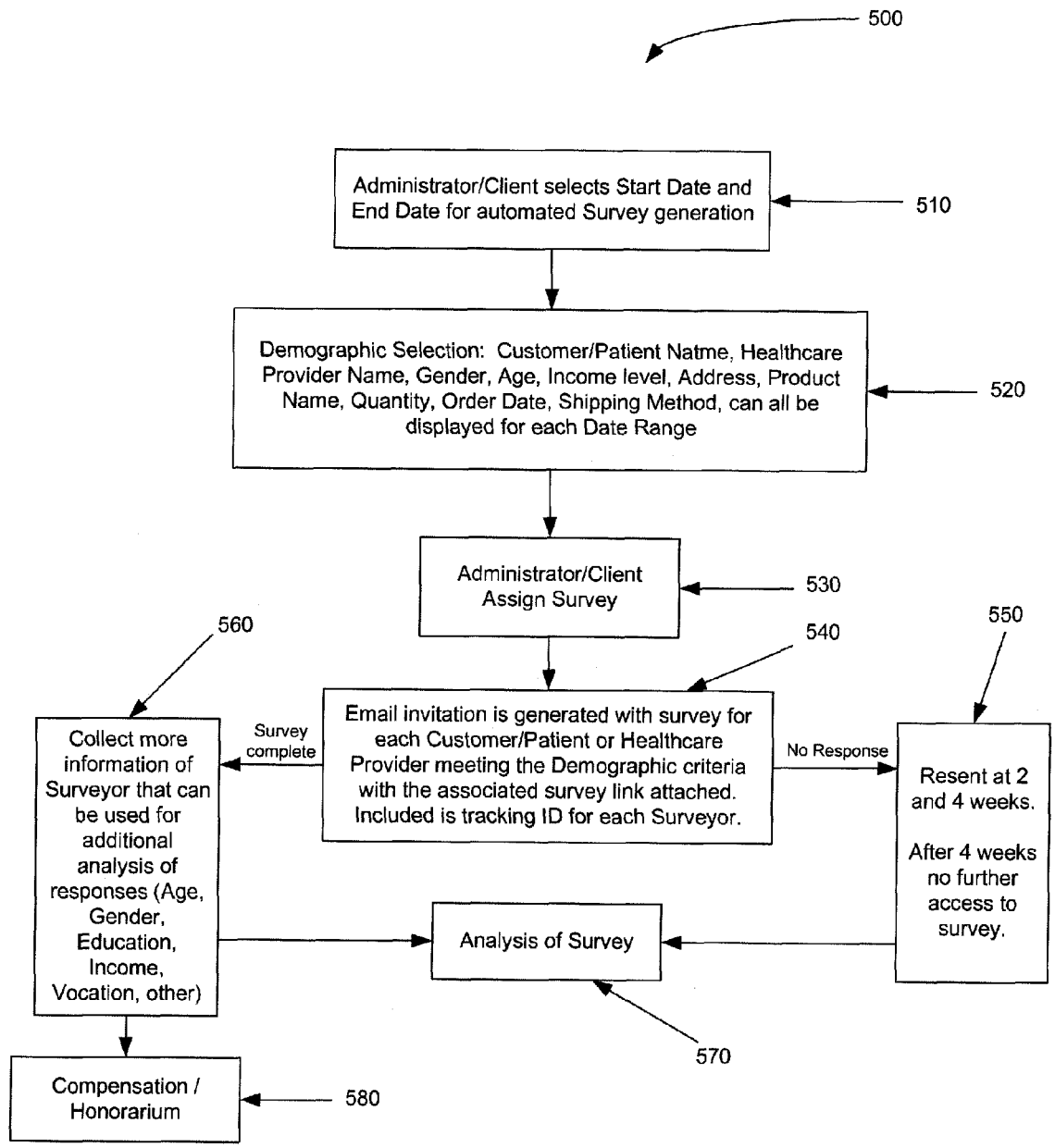
FIG. 5 is a flow chart diagram of the survey selection and data acquisition portions of the system of the invention.

FIG. 5 illustrates the survey selection and data acquisition portion of the system 500. The selector may select a start date and an end date for the survey 510. The selector then may select desired demographics for the patient 520. Such demographics may include the patient's name, healthcare provider's name, gender, age, income level, address, product name, quantity prescribed or recommended, order date, shipping method, and the like. A display may be provided for the selector to provide preselected demographic requirements for each date range selected at 510.

Once the demographic selection 520 has been completed, the selector then may assign surveys 530 to be sent to one or more healthcare providers, patients or both. An email invitation 540 may be generated with each survey created. The email 540 may contain a link to a website having the individually created survey. Additionally, a tracking ID may be included for each survey to confirm that the right person is responding to the right survey.

If no response is provided within a predetermined time limit, an email may be resent one or more times 550 to the healthcare provider or patient taking the survey. For example, follow up emails may be sent after 2 and 4 weeks. After another preselected time, the reminders may stop, and access to the website having the survey may be denied.

If, however, the survey is answered to a predetermined amount of completion, then additional information 560 may be obtained from the healthcare provider to aid in the analysis of the responses to the survey 570. An analysis 570 can then be made of the data obtained from the patient, and, if applicable, the healthcare provider. Once the survey work has properly been completed, the system then can credit the patient and/or the healthcare provider for any predetermined compensation or honorarium due 580 for participation.

Figure 6:
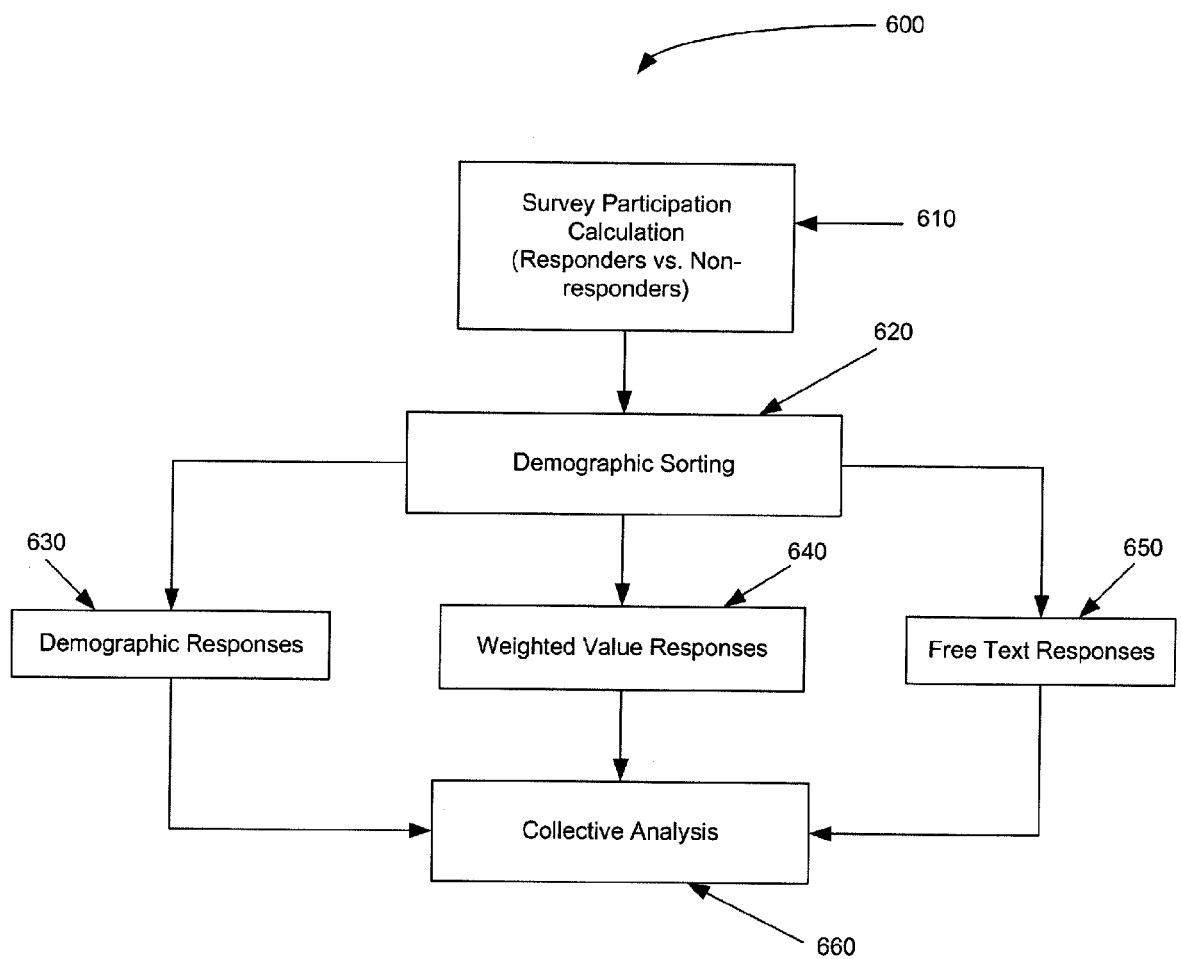
FIG. 6 is a flow chart diagram of the survey analysis portion of the system of the invention.

FIG. 6 provides a detail of the steps the considerations in the survey analysis 600. The analysis 600 may first include a calculation of responders versus non-responders 610. Then, sorting may occur by demographics 620. Once demographic sorting 620 is accomplished, the responses themselves are considered. The responses may include demographic responses 630 by the healthcare provider or patient, weighted value responses 640, and free text responses 650. Through the comparative analysis of the responses, a collective analysis 660 can be made.

Figure 7:
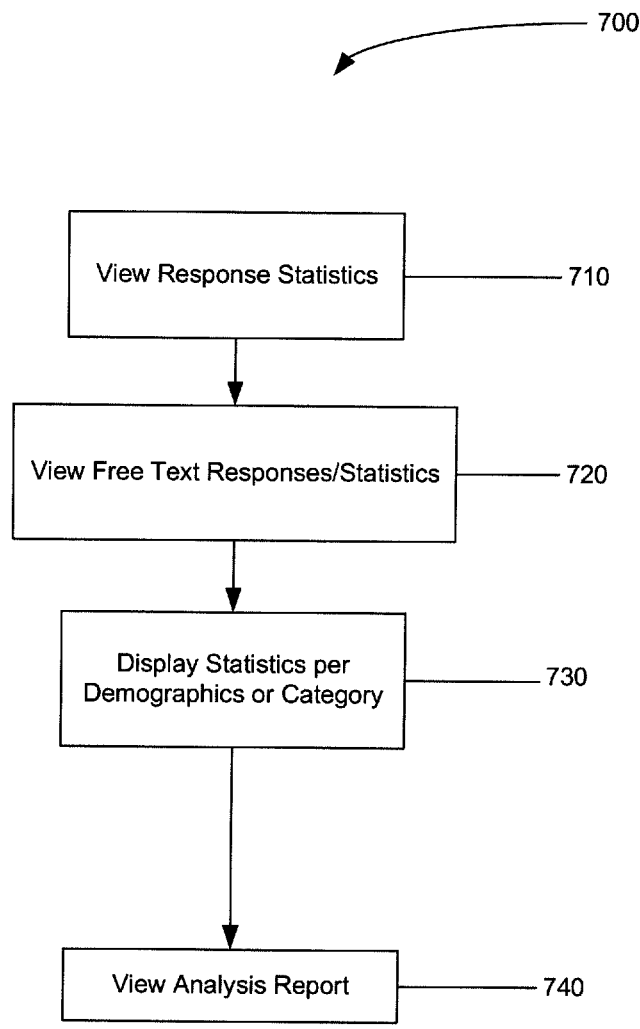
FIG. 7 is a flow chart diagram of the report generation portion of the system of the invention.

FIG. 7 provides a detailed flow chart of the report generation step of the system 700. The supplier or administrator may view response statistics 710 in total. Then, the system 700 may make available statistics related to free text responses 720 and related to demographics and/or category of the product surveyed 730. The statistics view analysis report 740 in this step may be printed out, displayed on a graphical user interface, or the like. Quickbooks and Excel and equivalent database management programs may be adapted to provide the reporting step of the system.

FIGS. 8*a*, 8*b* and 9 provide examples of surveys that may be generated by the invention 100. In FIGS. 8*a* and 8*b*, a survey 800 is shown providing choices for weighted value responses to questions related to a product.

In this example, the survey 800 is directed to the healthcare provider, and a free text field is provided for inclusion of the healthcare provider's comments relative to the patient or the patient's comments, if the patient has provided any. In this example, the product is a prenatal vitamin and supplement; however, other products may be the subject of the survey. Similarly, FIG. 9 shows a different survey 900 for obtaining information on calcium chocolate chews.

As noted above, a product may be altered based upon information obtained by the surveys of this system, and new analysis may be made on surveys regarding the altered product. Trends may be revealed as to the efficacy of different alterations which may not be obtained through other systems.

In operation of the system, emails may be sent to the healthcare providers with a link to the system to make access to the system easy and convenient. At the link forms may be provided by the system with questions, and free text fields to enter data collected may be provided to the healthcare provider. Once the forms are completed by the healthcare provider they may be sent via the computer communication system and analyzed. The analysis may be used in conjunction with the forms submitted by other healthcare providers relating to the same or similar products. The information obtained is utilized to enhance current products and create new innovative products.

It will be appreciated by persons skilled in the art that the present invention is not limited to what has been particularly shown and described herein above. In addition, unless mention was made above to the contrary, it should be noted that the accompanying drawings are not to scale. A variety of modifications and variations are possible in light of the above teachings without departing from the scope and spirit of the invention.

What is claimed is:

1. A method comprising:

transmitting, by a computer based system for managing healthcare information, a first on-line survey to healthcare providers based on a type of healthcare item associated with a health care provider, wherein the survey comprises a first request for information for a first attribute of the type of healthcare item and a second request for information for a second attribute of the type of healthcare item;

transmitting, by the computer based system, a second on-line survey to patients based on the type of healthcare item received by the patients, wherein each patient is associated with a patient profile, and wherein each patient profile is associated with the type of healthcare item and the health care provider;

receiving, by the computer based system, responses to the on-line surveys from the healthcare providers and the patients;

correlating, by the computer based system, the first online survey from the healthcare provider with the second online survey from the patient based on the patient profile into correlated survey data, wherein first subjective data from the first on-line survey and second subjective data from the second on-line survey are associated, and wherein first objective data from the first on-line survey and second objective data from the second on-line survey are associated;

sorting, by the computer based system, the correlated survey data based on a demographic selection associated with the patient profile;

consolidating, by the computer based system, the responses to the online surveys based on the type of healthcare item and the demographic selection;

collecting, by the computer based system, a plurality of responses to the first request for information to create a first collective analysis for the first attribute;

collecting, by the computer based system, a plurality of responses to the second request for information to create a second collective analysis for the second attribute; and determining, by the computer based system, an honorarium linked to at least one of the response to first request for information and the response to the second request for information.

2. The method of claim 1, further comprising transmitting, by the computer based system, a registration link to allow patients to link to associated healthcare providers.

3. The method of claim 2, wherein the transmitting the registration link is providing at least one of a toll free telephone number and a link on a webpage.

4. The method of claim 1, wherein the on-line survey is customizable by a product supplier.

5. The method of claim 1, wherein the on-line survey transmitted to patients having preselected demographics.

6. The method of claim 4, wherein text in questions in the on-line survey are fully customizable.

7. The method of claim 4, wherein questions in the on-line survey are given weighted values.

8. A non-transitory computer-readable storage medium having stored thereon sequences of instructions, the sequences of instructions including instructions which, when executed by a computer based system for managing healthcare information, cause the computer based system to perform operations comprising:

transmitting, by the computer based system, a first on-line survey to healthcare providers based on a type of healthcare item associated with a health care provider, wherein the survey comprises a first request for information for a first attribute of the type of healthcare item and a second request for information for a second attribute of the type of healthcare item;

transmitting, by the computer based system, a second on-line survey to patients based on the type of healthcare item received by the patients, wherein each patient is associated with a patient profile, and wherein each patient profile is associated with the type of healthcare item and the health care provider;

receiving, by the computer based system, responses to the on-line surveys from the healthcare providers and the patients;

correlating by the computer based system, the first online survey from the healthcare provider with the second online survey from the patient based on the patient profile into correlated survey data, wherein first subjective data from the first on-line survey and second subjective data from the second on-line survey are associated, and wherein first objective data from the first on-line survey and second objective data from the second on-line survey are associated;

sorting, by the computer based system, the correlated survey data based on a demographic selection associated with the patient profile;

consolidating, by the computer based system, the responses to the online surveys based on the type of healthcare item and the demographic selection;

collecting, by the computer based system, a plurality of responses to the first request for information to create a first collective analysis for the first attribute;

collecting, by the computer based system, a plurality of responses to the second request for information to create a second collective analysis for the second attribute; and determining, by the computer based system, an honorarium linked to at least one of the response to first request for information and the response to the second request for information.

9. The storage medium of claim 8, further configured to perform operations comprising transmitting, by the computer based system, a registration link to allow patients to link to associated healthcare providers.

10. The storage medium of claim 9, wherein the-on-line survey is customizable by a product supplier.

11. The storage medium of claim 10, wherein the on-line survey is transmitted to patients having preselected demographics.

12. The storage medium of claim 10, wherein text in questions in the on-line survey are customizable.

13. The storage medium of claim 10, wherein questions in the on-line survey are given weighted values.

14. A computer based system comprising:
a network interface communicating with a non-transitory memory;
the non-transitory memory communicating with a processor for managing healthcare information; and
the processor, when executing a computer program, is configured to:

transmitting, by the processor, a first on-line survey to healthcare providers based on a type of healthcare item associated with a health care provider, wherein the survey comprises a first request for information for a first attribute of the type of healthcare item and a second request for information for a second attribute of the type of healthcare item;

transmitting, by the processor, a second on-line survey to patients based on the type of healthcare item received by the patients, wherein each patient is associated with a patient profile, and wherein each patient profile is associated with the type of healthcare item and the health care provider;

receiving, by the processor, responses to the on-line surveys from the healthcare providers and the patients;

correlating, by the processor, the first online survey from the healthcare provider with the second online survey from the patient based on the patient profile into correlated survey data, wherein first subjective data from the first on-line survey and second subjective data from the second on-line survey are associated, and wherein first objective data from the first on-line survey and second objective data from the second on-line survey are associated;

sorting, by the processor, the correlated survey data based on a demographic selection associated with the patient profile;

consolidating, by the processor, the responses to the online surveys based on the type of healthcare item and the demographic selection;

collecting, by the processor, a plurality of responses to the first request for information to create a first collective analysis for the first attribute;

collecting, by the processor, a plurality of responses to the second request for information to create a second collective analysis for the second attribute; and determining, by the processor, an honorarium linked to at least one of the response to first request for information and the response to the second request for information.

15. The system of claim 14, further configured to transmit, by the processor, a registration link to allow patients to link to associated healthcare providers.

16. The system of claim 15, wherein the transmitting the registration link is providing at least one of toll free telephone number and a link on a webpage.

17. The method of claim 14, wherein the on-line survey is customizable by a product supplier.

18. The method of claim 14, wherein the on-line survey is taken for patients having preselected demographics.

19. The method of claim 14, wherein text in questions in the on-line survey are customizable.

20. The method of claim 19, wherein questions in the on-line survey are given weighted values.

* * * * *